United States Patent [19]
Firth et al.

[11] Patent Number: 5,437,647
[45] Date of Patent: Aug. 1, 1995

[54] DISPOSABLE SELF-SHIELDING ASPIRATING SYRINGE

[75] Inventors: John R. Firth, Wilsonville, Oreg.; Anthony R. Perez, Alhambra, Calif.

[73] Assignee: Safety Syringes, Inc., Arcadia, Calif.

[21] Appl. No.: 104,182

[22] Filed: Aug. 9, 1993

Related U.S. Application Data

[63] Continuation-in-part of Ser. No. 783,825, Oct. 29, 1991, Pat. No. 5,279,581, which is a continuation-in-part of Ser. No. 581,734, Sep. 12, 1990, Pat. No. 5,108,378, which is a continuation-in-part of Ser. No. 521,243, May 9, 1990, abandoned.

[51] Int. Cl.⁶ .............................................. A61M 5/00
[52] U.S. Cl. ................................... 604/110; 604/187; 604/198; 604/232; 604/263
[58] Field of Search ............... 604/232, 198, 192, 187, 604/263, 218, 189, 111, 110

[56] References Cited

U.S. PATENT DOCUMENTS

| | | |
|---|---|---|
| 2,925,083 | 2/1960 | Craig. |
| 3,046,985 | 7/1962 | Saenz. |
| 3,878,846 | 4/1975 | Rimbaud. |
| 4,171,699 | 10/1979 | Jones et al. ........................ 604/187 |
| 4,772,272 | 9/1988 | McFarland. |
| 4,915,701 | 4/1990 | Halkyard. |
| 4,957,490 | 9/1990 | Byrne et al.. |
| 4,990,141 | 2/1991 | Byrne et al.. |
| 5,104,386 | 4/1992 | Alzain ............................... 604/232 |
| 5,112,307 | 5/1992 | Haber et al.. |
| 5,116,319 | 5/1992 | van den Haak. |
| 5,163,917 | 11/1992 | Huefner. |

*Primary Examiner*—John D. Yasko
*Attorney, Agent, or Firm*—Lyon & Lyon

[57] ABSTRACT

The disclosure relates to a syringe with a protector case which holds a glass carpule and permits the injection of the fluid contained in the carpule into the patient. The syringe is molded of plastic or other suitable material which is sterilizable. The device comprises seven parts including a body, protector case, needle, needle cap, plug, plunger and harpoon. The major components of the device preferably are molded from a suitable plastic and may be clear or of a color like or similar to a surgical glove.

37 Claims, 15 Drawing Sheets

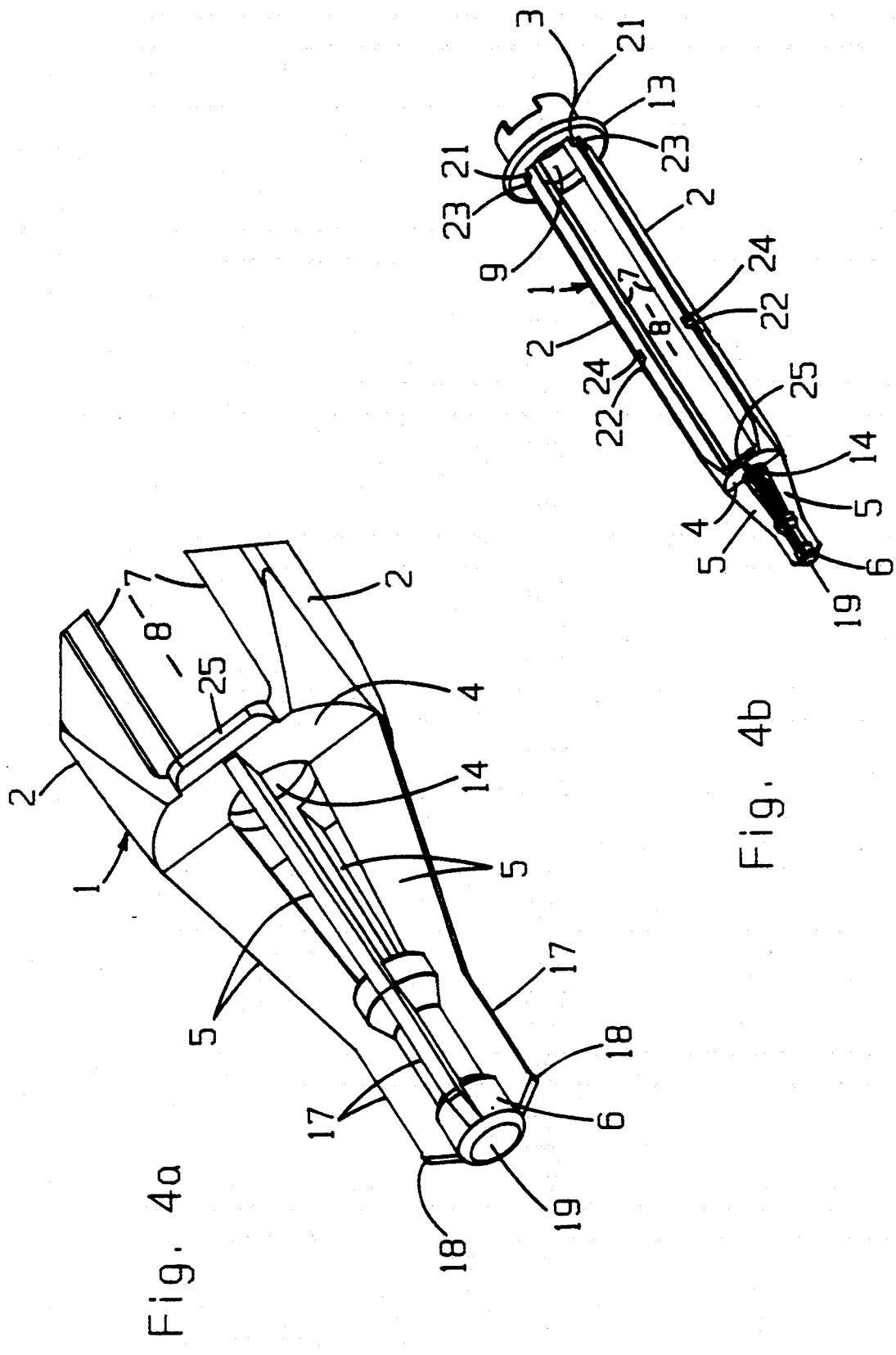

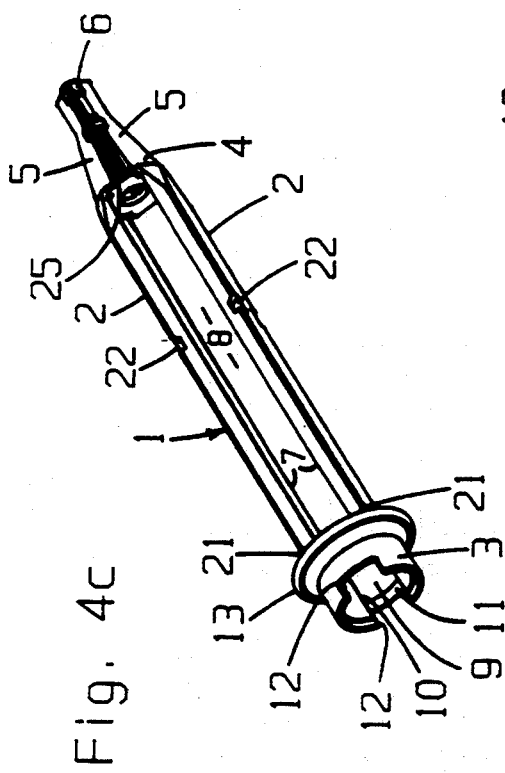
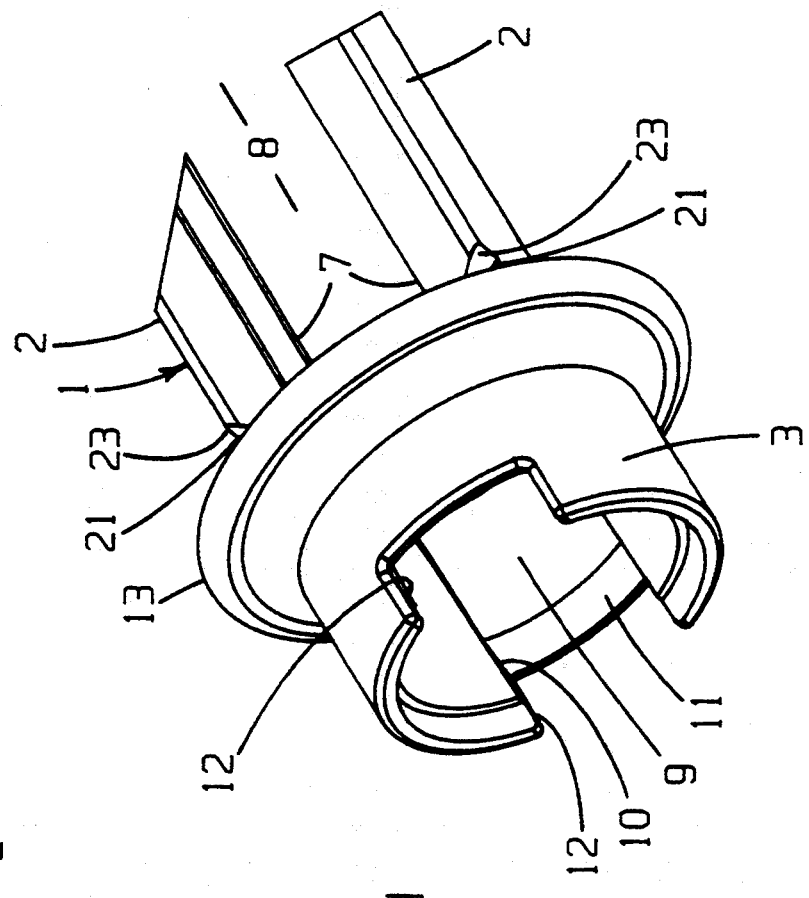
Fig. 4c
Fig. 4d

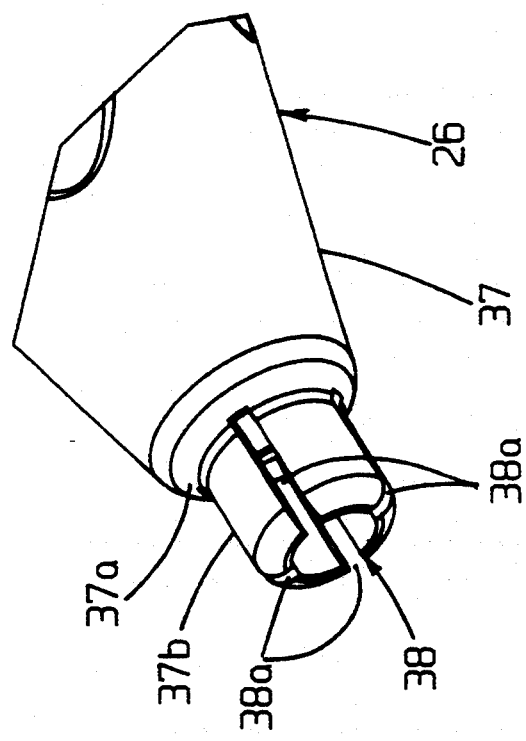
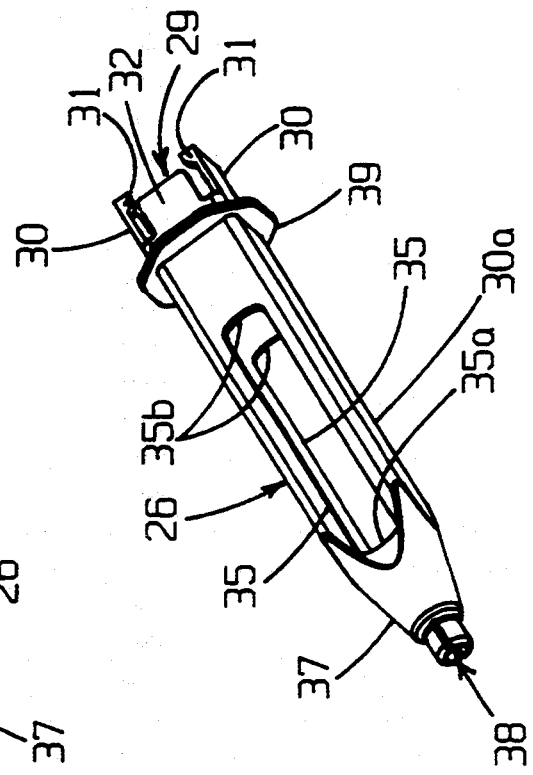
Fig. 5a
Fig. 5b

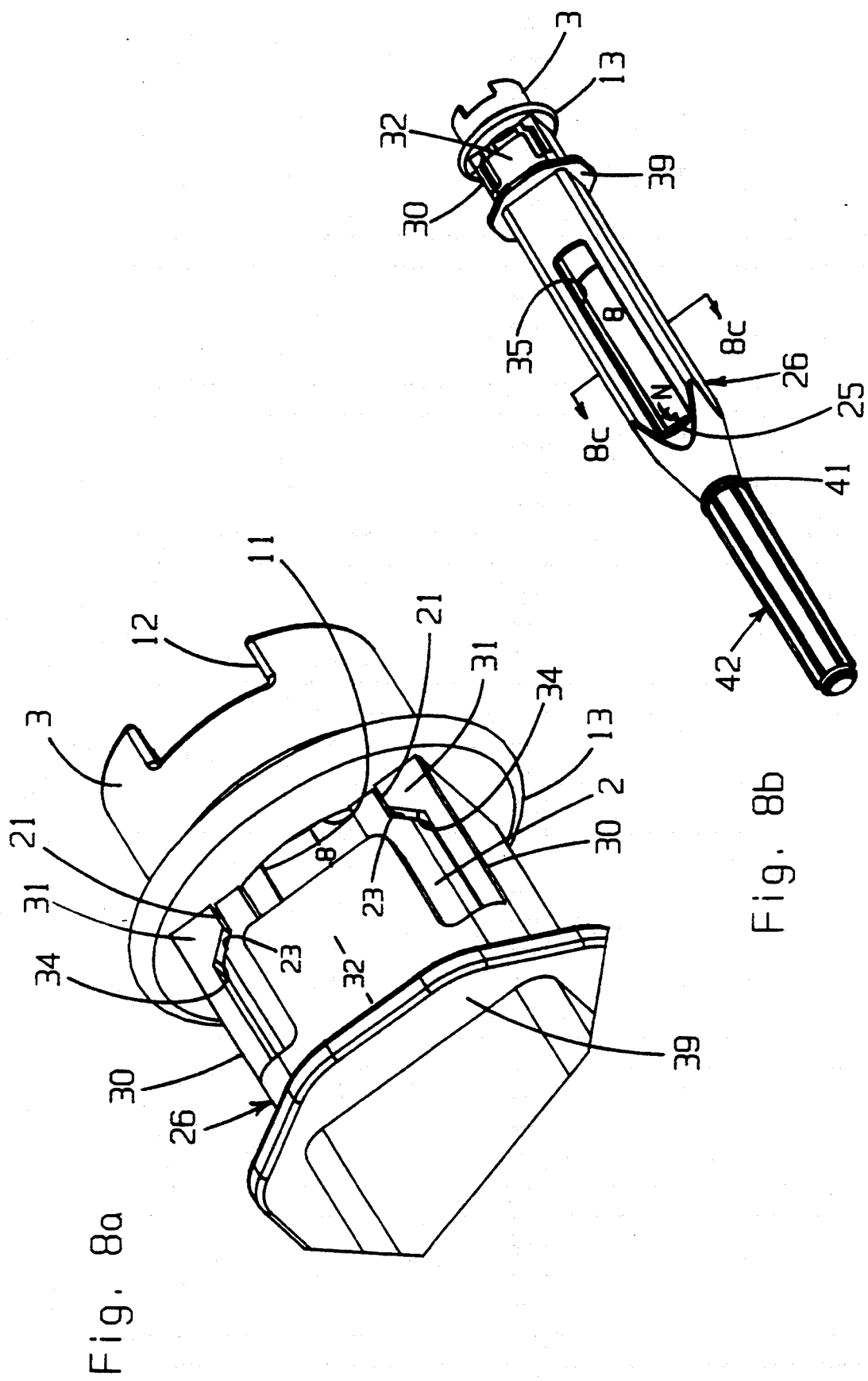

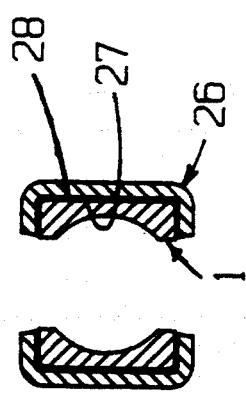
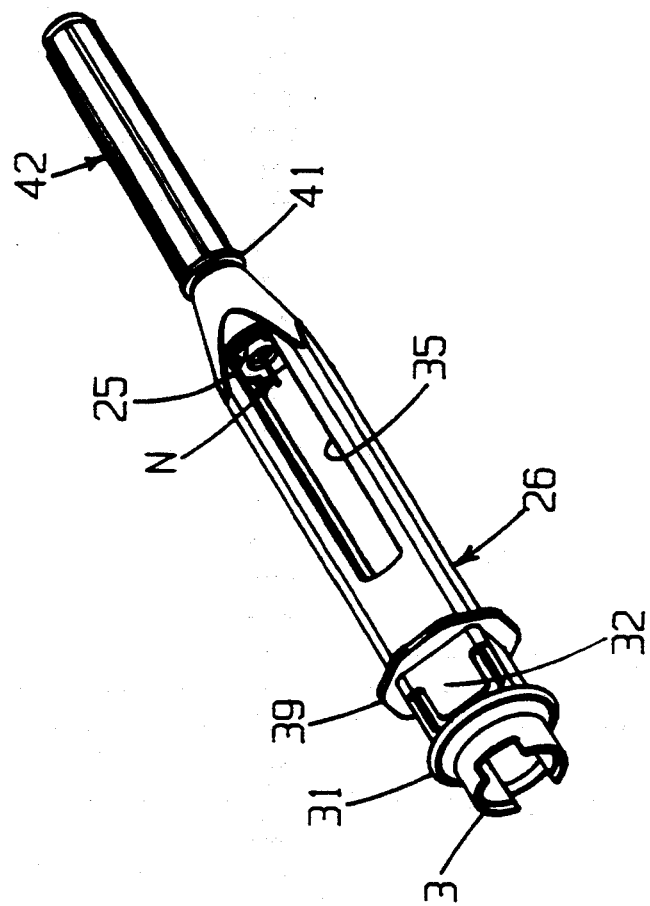

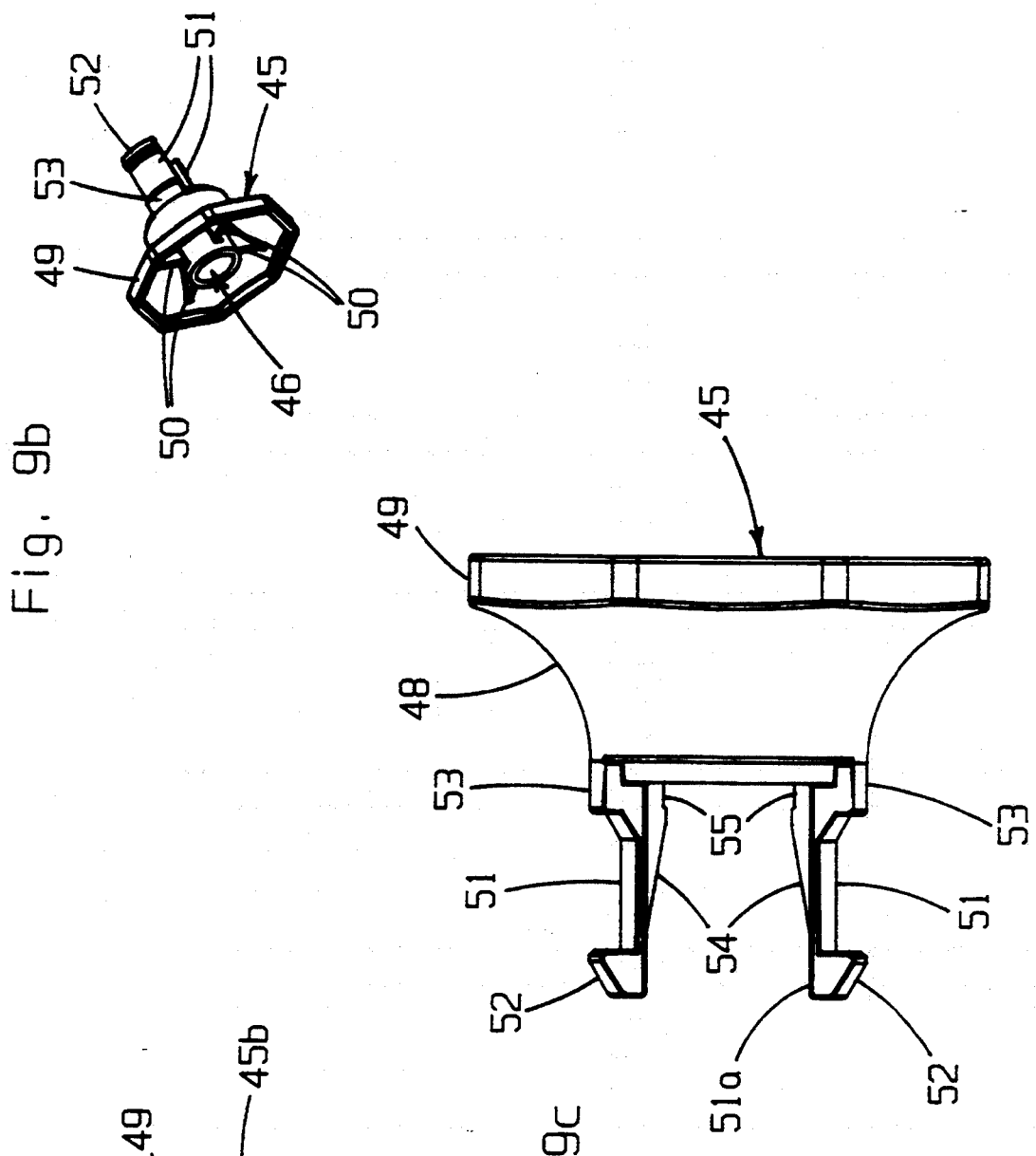

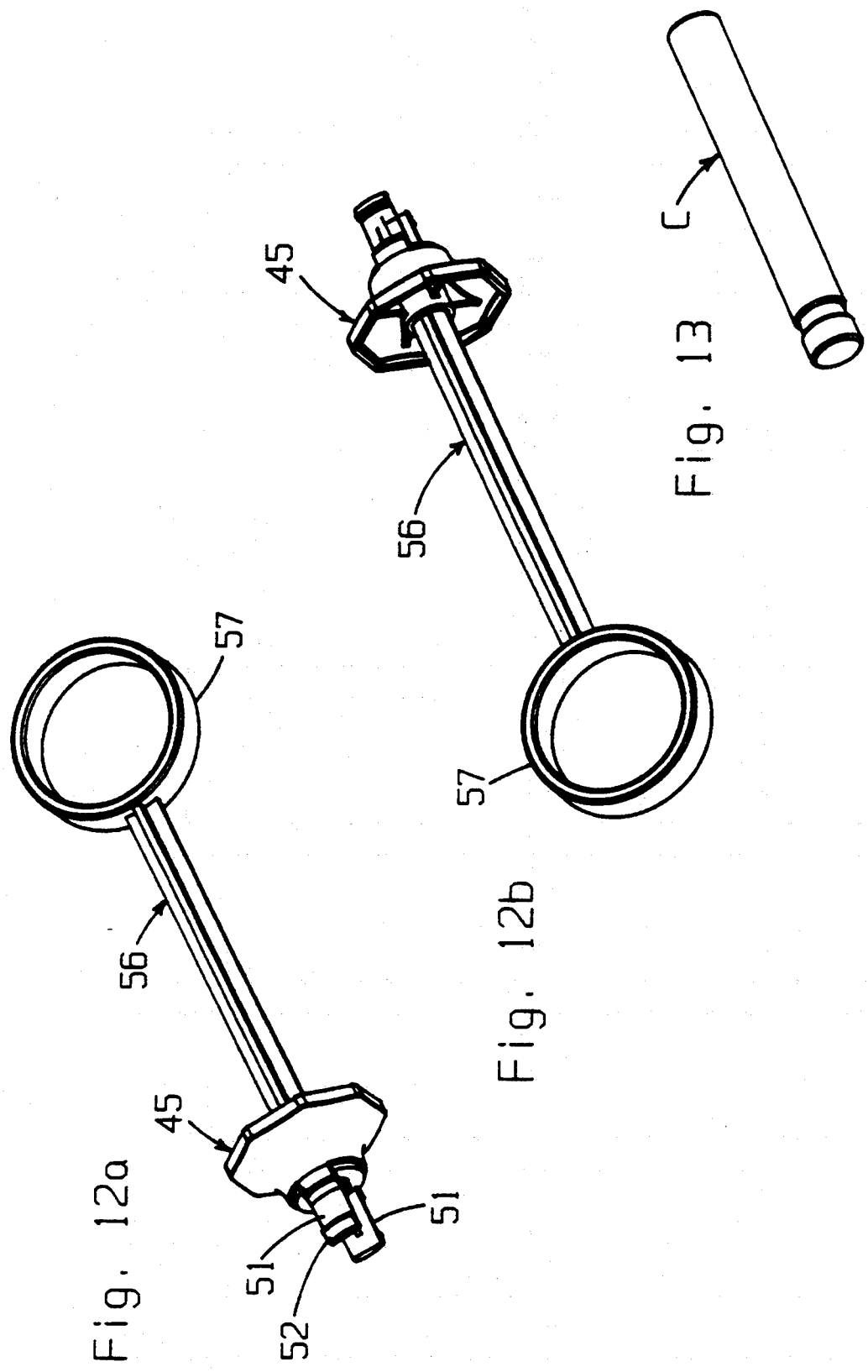

DISPOSABLE SELF-SHIELDING ASPIRATING SYRINGE

This is a continuation-in-part of application Ser. No. 783,825 filed on Oct. 29, 1991, now U.S. Pat. No. 5,279,581 which is a continuation-part of Ser. No. 581,734 filed Sep. 12, 1990, now U.S. Pat. No. 5,108,378, which was a CIP of application Ser. No. 07/521,243 filed on May 9, 1990, now abandoned.

BACKGROUND OF THE INVENTION

The increasing threat of AIDS has generated a rapid development of methods for preventing the spread of communicable diseases from the inadvertent reuse of needle devices, accidental needle stick injuries suffered by medical and dental practitioners, and ineffective sterilization of reusable devices. To be effective, the devices employed must be simple to manufacture and easy to use. U.S. Pat. No. 5,108,378 discloses a syringe having a rectangular body cross-section which permits the use of a protector case of matching interior cross section. The present application describes the application of many of the features of the above patent to the design of an aspirating syringe of the type in common use by dentists for the administering of local anesthesia and in a hospital environment for the administering of controlled substances. Both of these medications are normally packaged in glass carpules. A sterilized, single use, shieldable device for use with these carpules will extend the benefits of the self-shielded, disposable safety syringe to these applications.

Numerous attempts have been tried to solve the problems noted above with respect to aspirating syringes. Examples of prior art devices are found in the disclosures of the following U.S. patents.

U.S. Pat. No. 2,925,083 discloses a hood for concealing and guarding the needle of a syringe which may be easily retracted when the needle is inside the patient's mouth.

U.S. Pat. No. 3,046,985 discloses a sleeve adapter which conceals the needle and applies pressure to the gum tissue.

U.S. Pat. No. 3,878,846 discloses a dental type syringe with a disposable body and case, and a reusable finger grip and plunger. The case provides a sterile cover for the body and attached needle prior to use. The reusable finger grip allows the distance between the flanges of the finger grip to be adjusted.

U.S. Pat. No. 4,772,272 discloses an attachment for a reusable dental syringe which incorporates a sheath as part of the disposable needle assembly.

U.S. Pat. No. 4,915,701 discloses a reusable shield for attachment to a reusable dental syringe with a needle disconnect arrangement to enable disconnecting the needle with the shield in place.

U.S. Pat. No. 4,957,490 shows an injection device having a system for retracting a needle into the body using rearward motion of a plunger.

U.S. Pat. No. 4,990,141 discloses a disposable syringe for use with a carpule and having an elongated needle mount on the front of the body with a shield over the elongated mount.

U.S. Pat. No. 5,104,386 discloses a design of reusable, dental type syringe having a spring actuated, semicircular shield.

U.S. Pat. No. 5,112,307 discloses a reusable dental syringe with a slidable needle carrier. The needle carrier and needle are retracted into the body section by means of a plunger.

U.S. Pat. No. 5,116,319 discloses a disposable syringe with a system for retracting the needle into the body cavity by means of a plunger.

U.S. Pat. No. 5,163,917 discloses a separate add-on sheath for use with a standard reusable aspirating syringe.

SUMMARY OF THE INVENTION

The present invention relates to a syringe with a protector case which holds a glass carpule and permits the injection of the fluid contained in the carpule into the patient. The syringe is molded of plastic or other suitable material which is sterilizable. The device comprises seven parts including a body, protector case, needle, needle cap, plug, plunger and harpoon. The major components of the device preferably are molded from a suitable plastic and may be clear or of a color like or similar to a surgical glove.

The device is normally provided to the practitioner in two sub-assemblies. The body, protector case, needle, and needle cap make up the first sub-assembly. The plug, plunger, and harpoon make up the second sub-assembly.

The protector case is assembled with the case retracted over the body and the needle attached to the body and extending through an opening in the protector case. The needle is covered by the needle cap which is removably attached to the needle hub on the end of the body. The body and case have a rectangular cross section.

The harpoon is attached to the plunger and the plunger is inserted through a center tube of the plug with the harpoon positioned between locking fingers on the plug.

The two sub-assemblies are packaged together in a sealed container and sterilized.

The user removes the first sub-assembly from the package and inserts a selected medicine carpule into the open end of the body. The second sub-assembly is then positioned with the locking fingers of the plug engaging slots in the end of the body, and is pushed forward until the locking fingers clear the end of the slots and engage an interior surface of a finger grip on the body. The carpule has the usual rubber stopper, and the plunger is driven rapidly forward by the hand of the user or by striking on a hard surface to engage the harpoon in the rubber stopper of the carpule in a conventional manner. The needle cap is then removed and the syringe is ready for use. The engagement of the harpoon with the carpule rubber stopper permits the user to aspirate fluid from the patient by retracting the rubber stopper and to thereby determine if the needle has punctured a blood vessel.

After use, the protector case is slid axially forward over the needle end of the case until detents engage pockets on the edges of the body. In this position the needle is completely covered, obviating the need to recap the needle, and protecting those handling the device during disposal. Since the device is not intend for reuse there is no need to remove the contaminated needle nor to autoclave or otherwise resterilize the device.

The benefits of the invention are several, including the following:

1. The device is sterilized after packaging and used only once, ensuring the maximum protection for the patient and practitioner.

2. The device may be used with any medication available in carpules of the appropriate size.

3. The rectangular cross section of the body and protector case permit maximum exposure of the carpule for easy viewing of the carpule during aspiration and injection while providing the necessary rigidity of the device.

4. The rectangular cross section of the body and protector case make possible the use of a simple and effective detent mechanism for securing the protector case over the needle after use.

5. The protector case and single use/disposable nature of the device make it unnecessary to recap or remove the needle from the syringe eliminating exposure to the contaminated needle.

6. The device or at least selected portions thereof, can be molded of a suitably colored plastic and the appearance and feel of the molded syringe are less threatening to the patient resulting in more patient comfort.

7. The harpoon design makes penetration of the carpule rubber stopper more easily accomplished.

8. The plug design makes the two assemblies very easy to put together and difficult to disassemble.

It is thus an object of the present invention to provide an improved syringe.

BRIEF DESCRIPTION OF THE DRAWINGS

FIGS. 4a, 4b, 4c and 4d are perspective views of the body of the syringe.

FIGS. 5a, 5b, 5c and 5d are perspective views of the protector case.

FIGS. 8a, 8b and 8d are perspective views of the body and protector case sub-assembly showing in greater detail the manner in which the body and case are interconnected, and FIG. 8c is a cross-sectional view along a line 8c—8c of FIG. 8b.

FIGS. 9a and 9b are perspective views of the plug and FIG. 9c is an enlarged side view thereof.

FIGS. 12a and 12b are perspective views of the plug and harpoon sub-assembly.

FIG. 13 is a perspective view of a standard glass medicine carpule.

DETAILED DESCRIPTION OF THE PREFERRED EMBODIMENT

Figure 1:
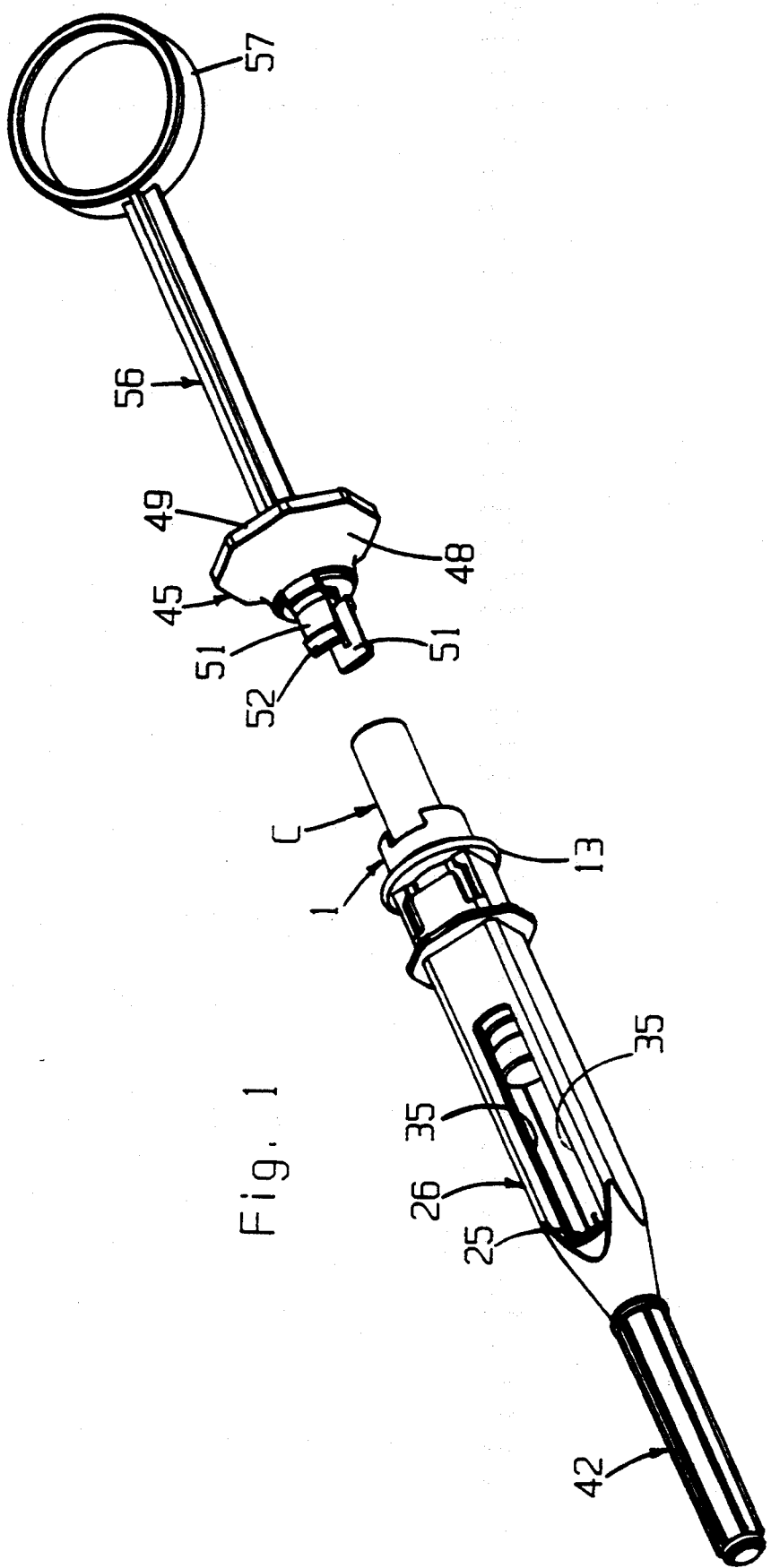
FIG. 1 is a perspective view of a syringe of the present invention in its unassembled state, with a carpule partially inserted, and showing the interrelationship of the various parts.
Figure 2:
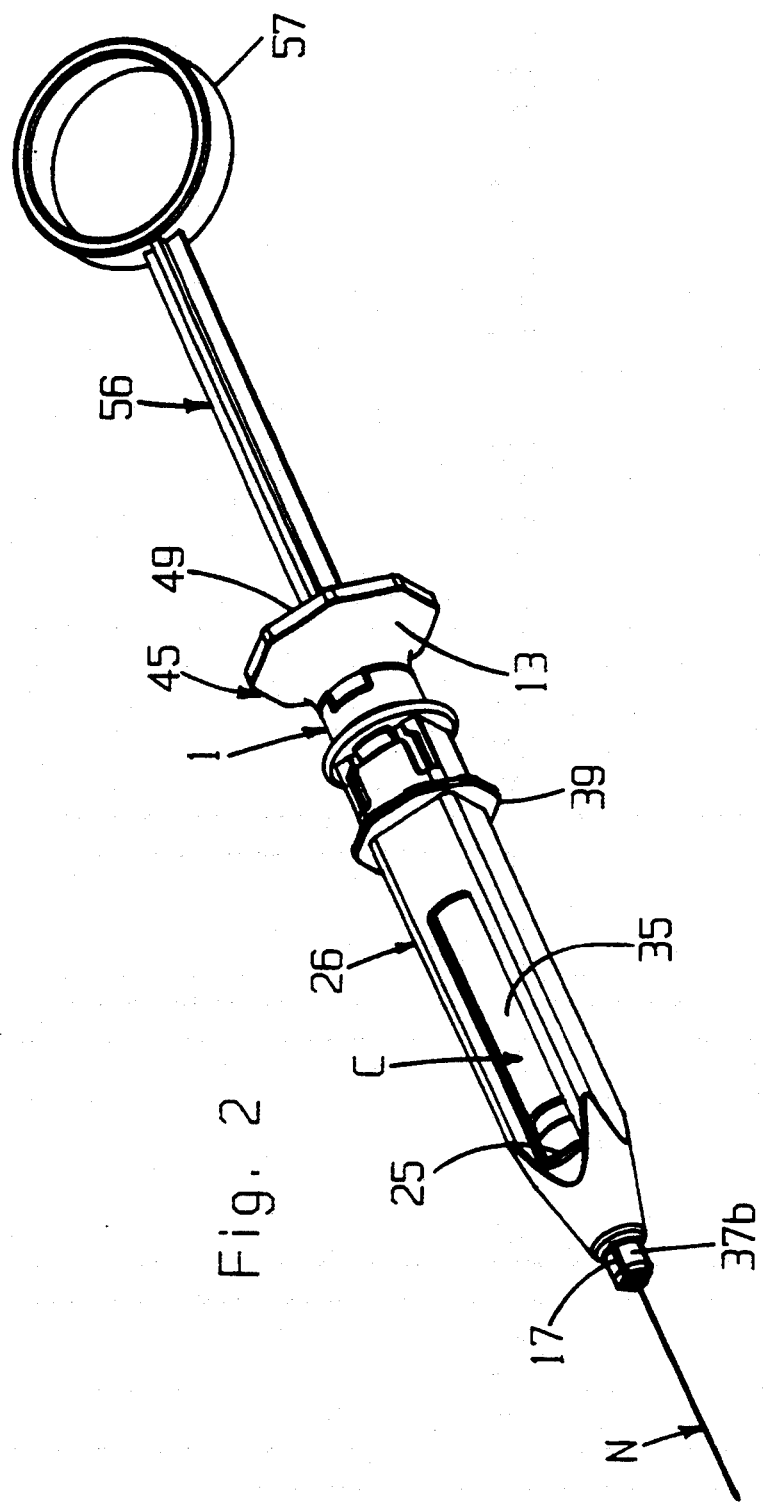
FIG. 2 is a similar perspective view of the syringe of the present invention in its assembled state, with a carpule, with the protector case in the retracted position, and the needle cap removed ready for use.
Figure 3:
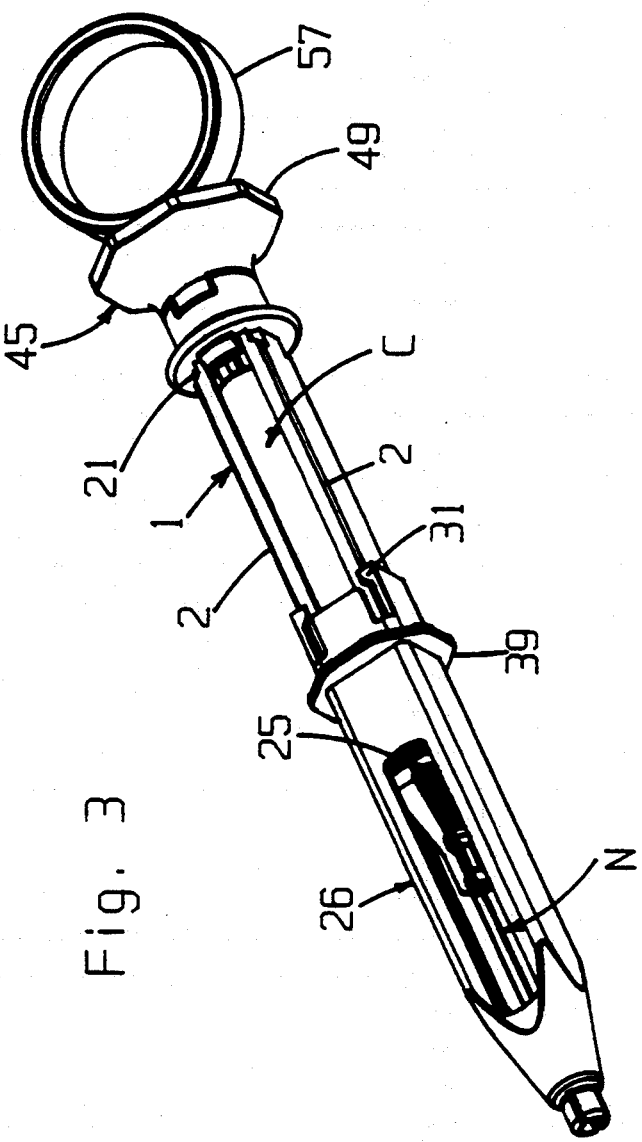
FIG. 3 is a similar perspective view of the syringe in its assembled state, with a carpule, but with the protector case in the extended (guarded) position ready for disposal after use.

As noted, FIG. 1 depicts the body and case sub-assembly with a standard medicine carpule C partially inserted in a cavity in the body, and the plug/harpoon sub-assembly oriented for movement axially to complete assembly of the device. FIG. 2 shows the device fully assembled with the needle cap removed to expose the needle, and FIG. 3 shows the device after use with the protector case in the forward (guarded) position ready for disposal.

Referring to those Figures and particularly to the detailed drawings of FIGS. 4a, 4b, 4c and 4d, the body 1 of the assembly has two elongated side rails 2 with a finger grip collar 3 integrally molded at one end of the side rails 2, and an end wall 4, needle hub support vanes 5, and needle hub 6 molded to the assembly at the opposite end of the side rails. The side rails 2 have interior concave surfaces 7 which conform to the outer diameter of the standard glass medicine carpule C (FIGS. 1 and 13) and form a carpule cavity 8. The outer edges of the side rails 2 define a rectangular cross-section 28 (see FIG. 8c) over which the protector case 26 is positioned. A circular opening 9 is provided through the finger grip collar 3 to permit passage of the carpule C during loading of the carpule into the cavity 8 of the body 1. Within the collar 3 are two tapered grooves 10 running axially along the interior surface of the collar 3. At the anterior end of these grooves are located two tapered pockets 11 which extend outward through the finger grip collar 3 to form two notches 12. These pockets 11 are shaped to receive the ends of two locking fingers 51 (FIG. 9) on the plug 45 when the plug sub-assembly is assembled to the body sub-assembly as will be described subsequently. The notches 12 provide easy orientation of the plug 45 for proper assembly to the body. The finger grip collar 3 has a forward finger grip ring 13 extending radially outward at the forward end of the collar 3 to permit the body 1 to be gripped during aspiration (which involves rearward thrust on the plunger 56 (FIG. 10a) and resultant rearward thrust on the body 1).

At the opposite end of the body 1, the end wall 4 forms the attachment between the two side rails 2 and provides the forward surface of the carpule cavity 8. On the forward surface of the end wall 4 the four needle hub support vanes 5 are attached and extend radially outward from core opening 14 and axially forward where they attach to the needle hub 6. The needle hub support vanes 5 have forward edges 17 parallel to the longitudinal axis of the body 1. These edges 17 interact with a needle cap 42 (FIG. 7) with the forward edges 17 engaging the interior surface 44a of the cap 42 to secure the cap 42 to the body 1. To further secure the needle cap 42 to the needle hub support vanes 5, there is a small radial protrusion 18 on the forward end of each edge 17 which has an interference fit with an interior bore 44a of the needle cap.

The needle hub 6 has a circular opening 19 extending through the hub 6. This opening 19 forms an adhesive pocket which extends axially into the hub from the end away from the body. The needle N (FIG. 6) is attached so that it extends through the annular opening 19 with the interior end of the needle extending past the end wall 4 and into the carpule cavity 8 to penetrate the forward end of the carpule C as is known in the art. The structure of the end wall 4, support vanes 5, and needle hub 6 are specifically designed and configured to facilitate cooling of the mold core during molding, and minimization of the plastic volume in this area of the body to improve heat transfer and reduce manufacturing cycle times. As an alternative, the hub 6 could be modified and have external threads to accommodate the present standard needle. This also would involve modification of the end of the case 26 to accommodate the modified hub 6.

Turning now to the other end of the body 1, rear detent pockets 21 are located on the outer edges of the side rail 2, adjacent to the forward end of the finger grip ring 13. These pockets 21 accept detents 31 (FIG. 5c) of the protector case 26 when the protector case is in the rearward (unguarded) position (see FIG. 2). Similarly formed forward detent pockets 22 are located on the outer edges of the side rails 2 at a distance from the rear detent pockets 21 such that, when the protector case detents 31 are engaged in the forward detent pockets 22, the forward end of the protector case covers the outward end of the needle as shown in FIG. 3. The rear detent pockets 21 have front surfaces 23 which are angled from the plane normal to the axis of the body to permit the detents 31 on the protector case 26 to be readily disengaged from the rear detent pockets 21 by sliding the protector case 26 forward. The forward detent pockets 22 have rear surfaces 24 that are in the plane normal to the longitudinal axis of the body 1 and which prevent the protector case 26 from being moved in a rearward direction when the protector case detents 31 are engaged in the forward detent pockets 22. The end wall 4 includes stop tabs 25 (FIG. 4a) which protrude from the top and bottom of the body 1 and interact with windows 35 (FIGS. 5a–b) in the top and bottom of the protector case 26 to limit the travel of the protector case 26 in the forward direction (note FIG. 3) and in the rearward direction (note FIGS. 2, 8b and 8d).

Figures 5C, 5D:
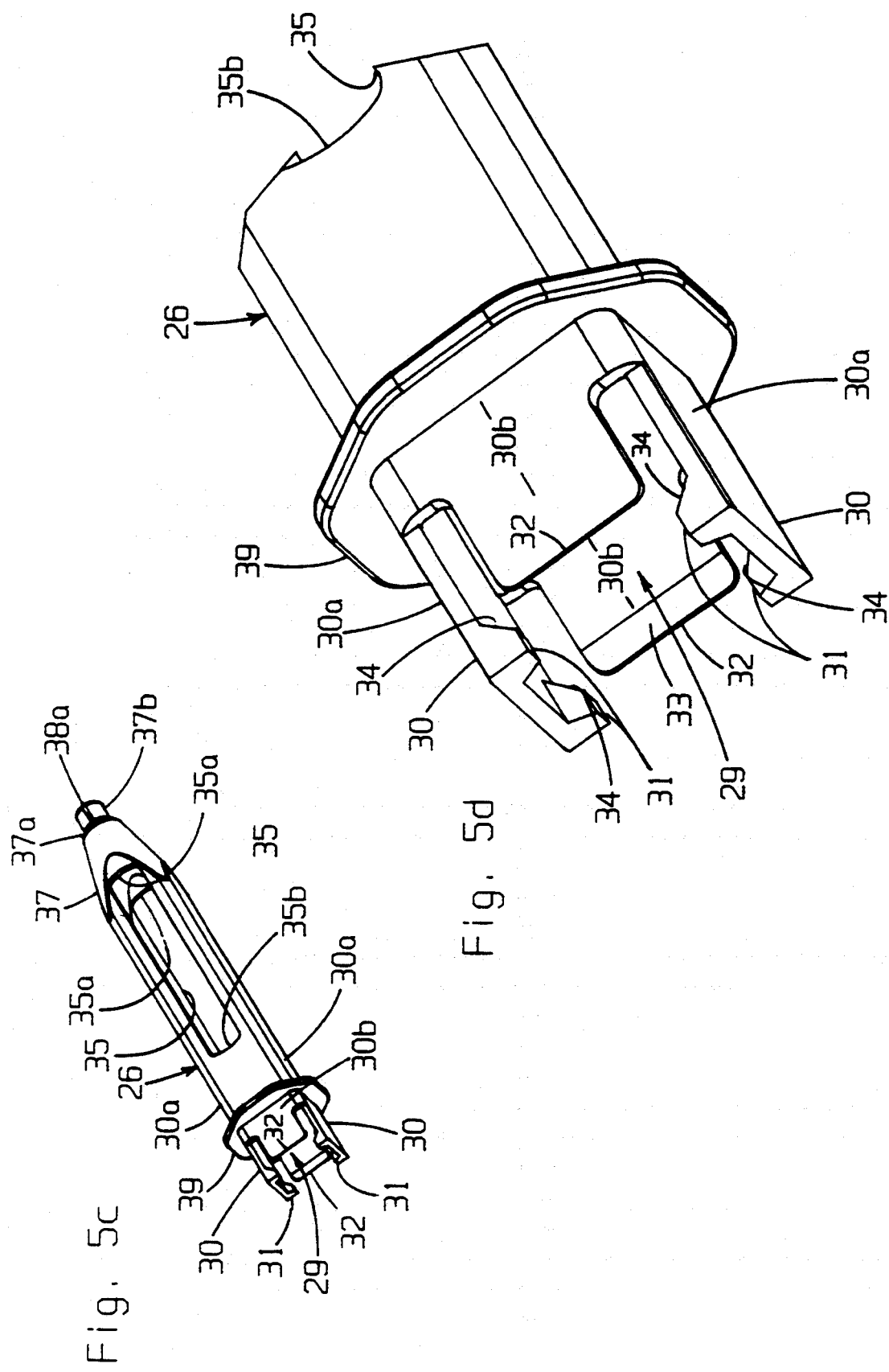

Referring now to FIGS. 5a, b, c and d, the protector case 26 comprises a tubular envelope with a rectangular internal cross-section 27 (see FIG. 8c) which conforms to the rectangular cross-section 28 of the body 1 as seen in FIG. 8c. The protector case 26 has an open rear end 29 with a pair of detent arms 30 and detents 31 integrally molded into side walls 30a. Assembly tabs 32 with tapered inner surfaces 33 are integrally molded into the top and bottom walls 30b to facilitate the assembly of the guard case 26 over the stop tabs 25 on the body 1. The detents 31 have sloped forward surfaces 34 (see FIG. 5d) which interact with the sloped forward surfaces 23 of the rear detent pockets 21 of the body 1 to disengage the detents from the rear detent pockets 21 of the body when the protector case 26 is slid forward. Two elongated windows 35 are positioned in the top and bottom walls 30b of the protector case 26 such that when the protector case 26 is in the rearward (unguarded) position as seen in FIG. 2, the forward edges 35a of the windows are in close proximity to the forward surfaces of the stop tabs 25 and when the protector case 26 is in the forward (guarded) position as seen in FIG. 3 the rearward edges 35b of the windows 35 are in close proximity to the rearward surfaces of the stop tabs 25 so that further forward motion of the protector case 26 is prevented by the interaction of the stop tabs 25 and rearward window edges 35b. The forward end of the protector case is formed into a cone 37 which transitions from the rectangular section of the protector case 26 which covers the side rail 2 area of the body 1 to a smaller diameter which covers the needle support vanes 5 (FIG. 4a). The forward end of the case 37 terminates in a collar 37a (FIG. 5a) to a sleeve 37b. The sleeve 37b has a smaller diameter than the edges 17 of the needle hub support vanes 5. The sleeve 37b has four slots 38a which permit the sleeve 37b to be drawn over the hub 6 with the edges 17 protruding through the slots 38a in the sleeve 37b. This arrangement permits the cap to be attached directly to the edges 17 of the body 1 while maintaining a small diameter 38 at the end of the protector case 26.

The protector case 26 has an actuator ring 39 molded to the protector case 26 in the area between the rear edges 35b of the windows 35 and the forward end of the detent arms 30. The ring 39 extends radially outward from the outer surface of the protector case 26 with the outer edges defining an octagonal shape as best seen in FIG. 5d.

Figure 6:
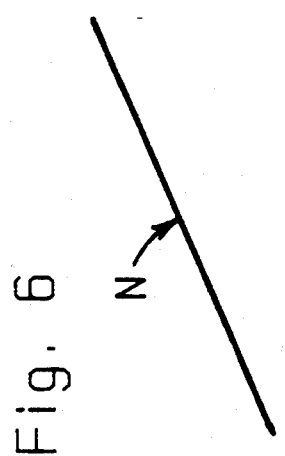
FIG. 6 is a perspective view of the needle.

The needle N shown in FIG. 6 is a standard metal cannula, having a hollow passageway through its length for the passage of fluids. The forward end is sharpened to permit penetration of the patient's tissue and the rear end is sharpened to permit penetration of the rubber membrane on the forward end of the medicine carpule C. The needle N is affixed within the needle hub 6 by adhesive during the manufacturing process. Alternatively, the hub 6 of the body 1 can be threaded to receive the present standard needle.

Figure 7A:
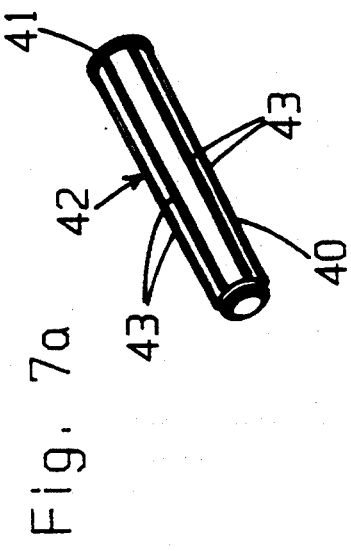
FIGS. 7a, 7b and 7c is are perspective views of the needle cap.
Figure 7B:
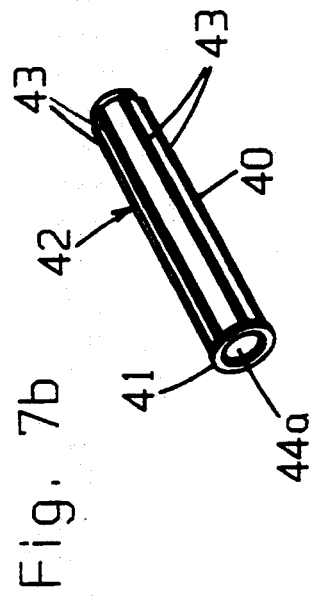
Figure 7C:
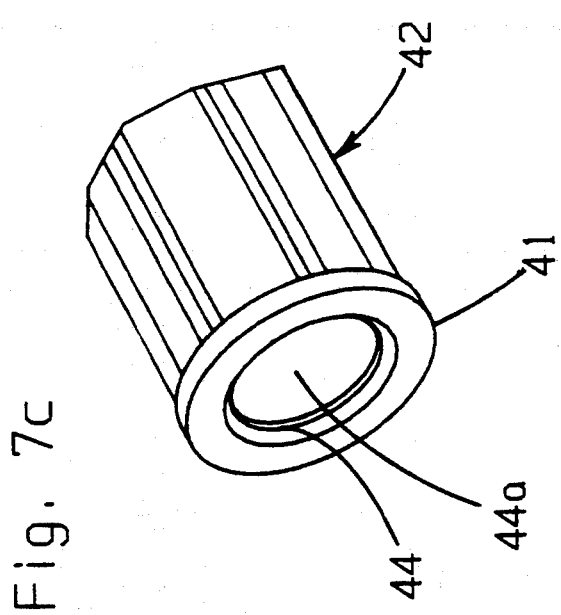

The needle cap 42 as shown in FIGS. 7a, b, c has a tapered section 40 with a ring 41 on its rear end. The tapered section 40 is closed at the forward end and has axial ribs 43 on its exterior surface. The ring 41 extends radially from the longitudinal axis and provides a means of stripping the mold and indexing in the manufacturing process. The inside surface 44a of the cap 42 is parallel to the longitudinal axis of the cap 42 for a distance approximately equal to the length of the forward edges 17 (FIG. 4a) of the needle support vanes. On the rear end of the interior surface there is a raised ring 44 of slightly smaller diameter which has an interference fit with the forward edges 17 (FIG. 4a) of the needle hub support vanes 5. This ring 44 enhances the attachment of the cap 42 to the needle hub support vanes 5 and also assists in stripping the molds in the manufacturing process.

These components are assembled into the body sub-assembly as shown in FIGS. 8b, c, and are shipped to the end-user with the protector case 26 in the rearward position as shown and the needle cap 42 in place over the needle. FIG. 8a particularly shows how the detents 31 of the cover 26 fit within the detent pockets 21 of the body 1.

Referring to FIGS. 9a and b, the plug 45 is shown and has an inner sleeve 45a with cylindrical opening 46 passing through it. An outer flared section 45b is molded to the forward end of this sleeve 45a at a face 47 and forms a rear finger grip 48. The outer edge 49 of this rear finger grip 48 has an octagonal shape 49 which, in conjunction with the octagonal protector case actuation ring 39 and rectangular protector case section 26, substantially prevents rolling of the syringe when placed on a flat surface. Radial vanes 50 are molded between the inner sleeve 46 and rear finger grip 48 to improve the rigidity of the plug.

Locking fingers 51 are molded to the face 47 of the plug 45 and extend axially forward. Locking detents 52 are located at the ends of the locking fingers 51. At the face end of each locking finger 51 is a base section 53 which contains the material required to fill the notches 12 (FIGS. 4c–4d) in the finger grip collar 3 of the body 1 so that, when the plug and body are assembled, the finger grip area has a smooth, comfortable surface. The inner surface 51a of each locking finger 51 has a stiffener rib 54 running normal to the surface beginning at the face 47 and tapering out at approximately two-thirds of the length of the locking finger 51. At the face end of each stiffener rib 54 there is a recess 55 which interlocks with a plunger end cap 58 (FIG. 10a) to provide a positive positioning of the two parts while in the sub-assembly condition. The outer surfaces of the locking fingers 51 and locking detents 52 are equidistant from the longitudinal axis of the plug 45 which maintains more uniform wall thicknesses in the mating sections 10, 11 and 12 of the finger grip collar 3 of the body 1.

Figure 10A:
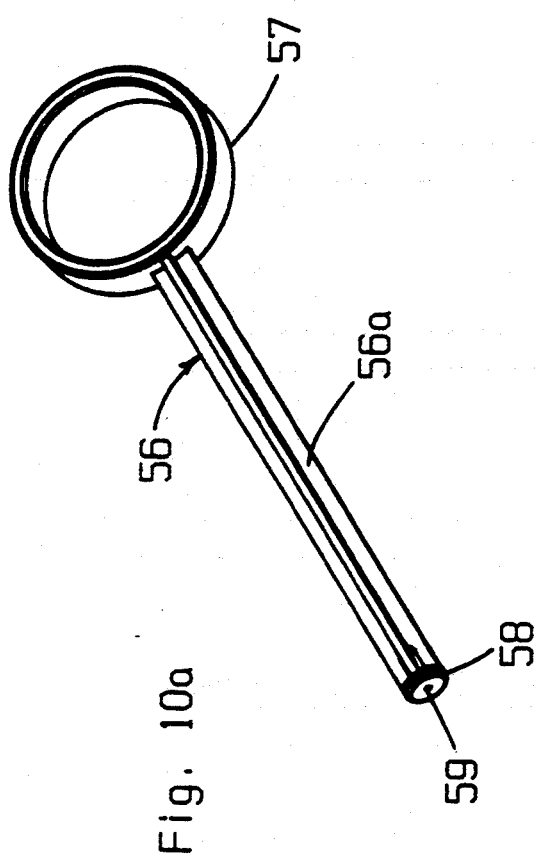
FIG. 10a is a perspective view of the plunger.
Figure 10B:
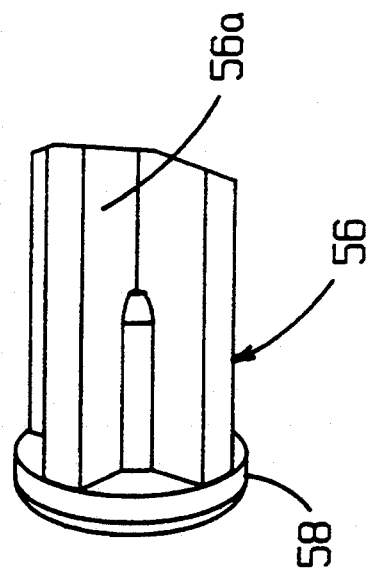
FIG. 10b is an enlarged view of the harpoon end of the plunger.

Referring to FIGS. 10a, b the plunger 56 has an elongated column 56a of cruciform cross section with a thumb ring 57 on the rearward end, and the end cap 58 on the forward end. A harpoon recess 59 extends from the forward face of the end cap 58 rearward along the axis of the column 56a. The wall area around this recess is thickened as shown in FIG. 10b to provide strength.

Although the plug 45 could be designed with threads to engage similar threads on the body 1, the locking finger 51 arrangement is preferred. These fingers 51 are flexible so that the plug 45 and body 1 can be quickly and easily assembled by pushing the finger 51 end of the plug into the opening 9 (note FIG. 4d) of the body 1, and the finger 51 structure is simpler and cheaper to mold. A threaded connector between the plug and body would allow the two to be easily separated, which is undesirable; whereas, with the presently described construction with fingers 51 the two are not at all easy to separate. When the fingers 51 are snapped in place in the body and subsequently the plunger is pushed forward to push the harpoon into the rubber stopper of the carpule C, it is very difficult to then remove the plug 45 from the body because retracting the plunger 56 pulls the rubber stopper of the carpule C back and thus it would be necessary for the user to compress both the carpule stopper and the fingers 51 of the plug 45 in order to get the plug 45 loose from the body. This provides an important safety feature as can be appreciated. Furthermore, the end cap 58 (note FIGS. 10a–10b) of the plunger 56 preferably has a slightly larger diameter than the hole 46 in the plug 45 to prevent the plunger 56 from being pulled out of the plug 45 (the front edge of the end cap 58 is tapered or chamfered as best seen in FIGS. 10b to thereby allow the end cap 58 to be assembled by insertion through the hole 46 in the plug 45.

Figure 11:
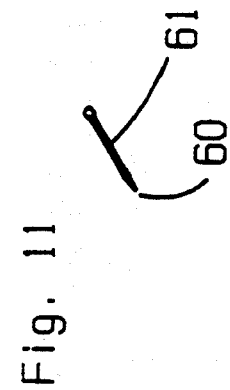
FIG. 11 is a perspective view of the harpoon.

The harpoon is shown in FIG. 11 and is a metal shaft with a pointed end 60 and a barb 61. The shaft is deformed at the other end in any suitable way to provide resistance to retraction after the shaft is forced into the harpoon recess 59 in the plunger 56.

The plug 45, plunger 56, and harpoon are assembled into the plug sub-assembly as shown in FIGS. 12a, b, and are shipped in this form with the body sub-assembly. After use, the entire syringe assembly, including the needle N is disposed of.

Except for the harpoon and needle, the above described components are injection molded using conventional techniques. The material preferably is an injection moldable plastic of the type used for sterilizable medical devices, such as polypropylene.

Another advantage, in addition to simplifying manufacture and providing a readily disposable syringe, in molding the syringe components (other than the needle and harpoon) from plastic is that if the syringe body contacts the skin of the patient, the syringe does not feel cold to the touch as with conventional metal aspirating dental syringes. Furthermore, and of particular importance, is the fact that the syringe components can be molded from a colored plastic or otherwise colored and, significantly, can be molded of a color which is the same as or similar to the color of surgical gloves (typically an ivory color). By providing this particular color, at least for the portions seen by a patient (i.e., the ring 57 and possibly the plug 45), the color of the syringe blends into the color of the glove and becomes essentially an extension of the physician's hand and therefore appears to be less obtrusive or threatening to the patient.

Figure 14A:
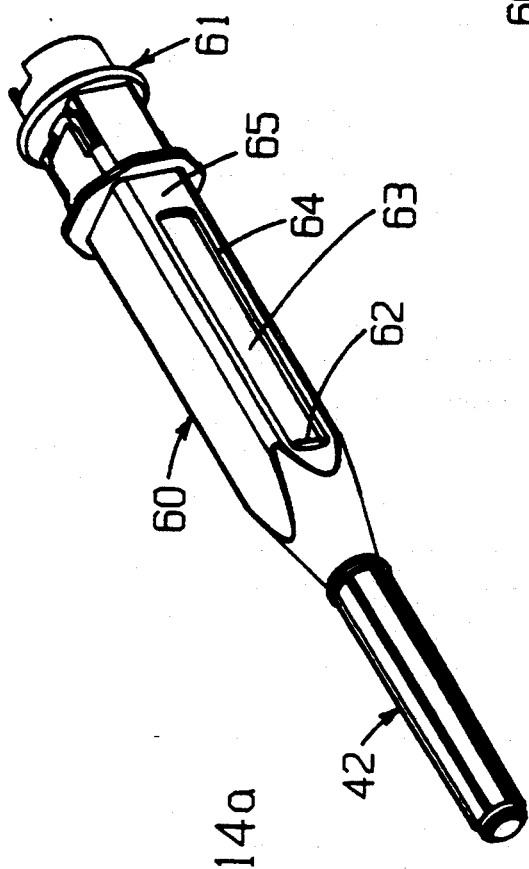
FIGS. 14a, b and d are perspective views of a second preferred embodiment of the body and protector case sub-assembly showing an alternative arrangement of the windows in the protector case and the stop tabs on the body.
Figure 14B:
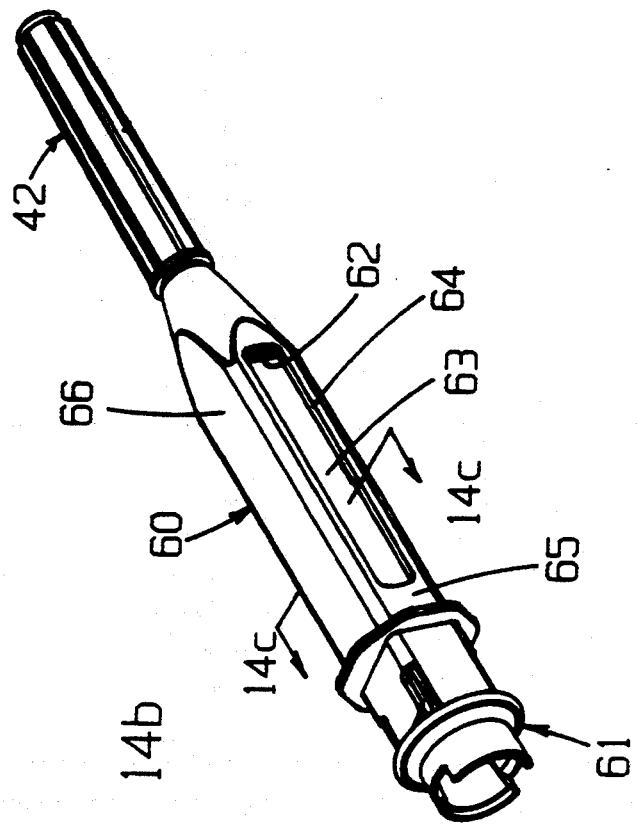
FIG. 14c is a cross-sectional view along a line 14c—14c of FIG. 14b.

Referring to FIGS. 14a, b, c and d, an alternative preferred embodiment is shown which provides a complete encapsulation of the carpule while the protector case is in the unguarded position. This configuration has the advantage of protecting the dentist and patient from glass fragments should the carpule shatter during preparation or use of the syringe. The disadvantage of this configuration is that the encapsulation reduces the visibility of the carpule and its contents during aspiration.

Figure 14C:
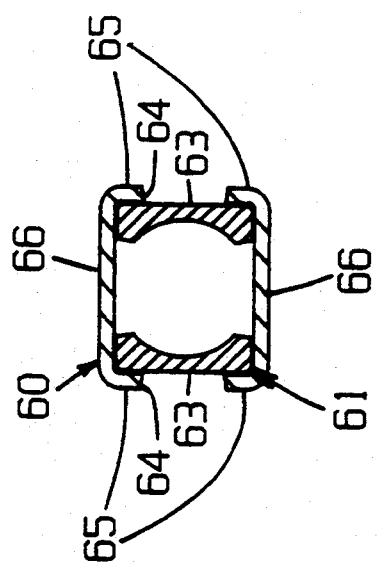

FIGS. 14a and b show the modified protector case 60, modified body 61, and needle cap 42 sub-assembled in the pre-use configuration. The stop tabs 62 are located on the side walls 63 of the body. The windows 64 are located in the sidewalls 65 of the protector case. The stop tabs 62 and windows 64 function in the same way as described earlier to limit travel of the protector case. FIG. 14c is a cross-section at line 14c—14c and shows the top and bottom of the protector case 60 covering the openings in the body 61.

Figure 14D:
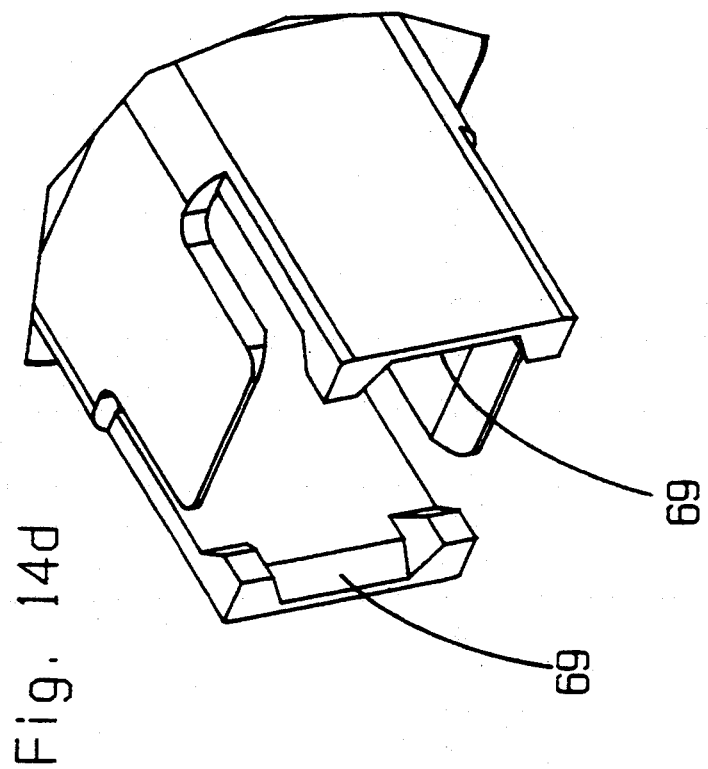

Tapered inner surfaces 69 (FIG. 14d) are provided on the ends of the detent arms between the detents to facilitate assembly of the protector case over the stop tabs on the sides of the body.

DESCRIPTION OF THE ASSEMBLY AND OPERATION OF THE PREFERRED EMBODIMENT

The syringe device of the present invention is assembled at the manufacturing facility into the two sub-assemblies as shown in FIGS. 8 and 12. These sub-assemblies are placed together and sealed in a suitable container which provides a microbial barrier. The packaged devices are then sterilized by gamma radiation and shipped to the end user either directly or through a distribution chain.

Immediately prior to use, the container is opened and the body sub-assembly shown in FIG. 8 is removed. The carpule C of FIG. 13 containing the selected medication is next inserted into the carpule cavity 8 as seen in FIG. 4. The plug sub-assembly of FIG. 12 is then removed from the container and the locking fingers 51 are aligned with the notches 12 (see FIG. 4d) in the finger grip ring 3 of the body 1. The plug 45 is pushed forward until the detents 52 of the locking fingers 51 engage the forward wall of the finger grip ring 13. As the locking fingers 51 move forward, the front end of the locking fingers 51 push against the rear surface of the carpule C forcing the carpule forward over the rear end (see FIG. 8d) of the needle N which penetrates the standard rubber seal on the forward end of the carpule C in a conventional manner.

The plunger 56 is moved forward until the pointed end of harpoon contacts the rear surface of the rubber stopper at the rear of the carpule C. The plunger 56 is then forced sharply forward by striking the finger ring 57 with the palm of the hand of the user or against a hard surface in a conventional manner. This imbeds the harpoon in the rubber stopper with the barb engaged.

The needle cap 42 is then removed and the needle inserted into the patient. The rubber stopper of the carpule C is then moved rearward by retracting the finger ring 57 of the plunger 56 to draw body fluid into the carpule C (aspiration) in the usual way to determine if the needle N has penetrated a blood vessel, and if not the plunger 56 is pushed forward to discharge the medication contained in the carpule C into the patient.

After injection, the needle is retracted from the patient. As the syringe is withdrawn the protector case 26 may be grasped with the free hand of the user and held as the syringe is moved away from the patient thus sliding the protector case 26 forward over the needle N and into the guarded position as shown in FIG. 3. Alternatively, the protector case 26 may be operated with one hand by moving the index and middle fingers forward between the rear of the protector case actuator ring 39 and front of the finger grip ring 13 moving the thumb rearward in the ring 57 thereby drawing the body 1 rearward into the protector case 26. As the protector case 26 slides forward, the detents 31 engage the forward detent pockets preventing subsequent rearward movement of the protector case 26. The stop tabs 25 and rear edges 35b of the windows 35 provide a positive stop when moving the protector case 26 forward to cover the needle. The entire device is then disposed of without further exposure of the needle or other action required.

The improvements which are the particular subject of the present invention are:

1. A cross-sectional shape which retains the rectangular shape of the body exterior and protector case interior while permitting the body to be molded with a window in the top and bottom for viewing the carpule during operation.

2. A configuration of the detents and detent pockets which permits the body to be molded with a window in the top and bottom for viewing the carpule during operation.

3. A modified interior cavity in the body which permits insertion and retention of a carpule containing medication.

4. A rear finger grip area on the body which provides an area for gripping the syringe during aspiration.

5. A simple, easily aligned and attached plug for closing the rear opening of the carpule cavity in the body while providing an effective finger grip for injecting medication.

6. A molded syringe of plastic and with components of a color the same as or similar to a surgical glove.

7. A structure to permanently affix a needle to the body which facilitates the molding of the body and enables high production rates to be maintained by providing adequate cooling.

8. An arrangement to removably attach a needle cap for protection of the needle prior to use.

9. A plunger design which includes a harpoon recess for attaching the harpoon to the plunger.

While embodiments of the present invention have been shown and described, various modifications may be made without departing from the scope of the present invention, and all such modifications and equivalents are intended to be covered.

What is claimed is:

1. A disposable self-shielding aspirating syringe comprising a body having a cavity for receiving a medical carpule, the body having a first forward end with a needle for penetrating a carpule and for injecting medicine into a patient, and the body having a second collar end into which the carpule can be inserted, a protector case adapted to slidably fit on the body, and having a first open end through which the needle may extend and a second end wherein the second end of the case and the body have cooperating detents for facilitating placement of the case with respect to the body for uncovering and covering, respectively, an exposed end of the needle, and the case further comprising at least one elongated window opening for allowing the carpule to be viewed in the body through the window, the window having first and second ends, and the body having a tab for extending through and engaging at least one of the ends of the window, and a plug and plunger assembly comprising a plug for cooperatively mating with the collar end of the body and plunger which is movable with respect to the plug and body for causing medicine from the carpule to be administered through the needle.

2. A syringe as in claim 1 wherein the exterior of the body and the interior of the case each have a substantially rectangular cross-section.

3. A syringe as in claim 2 wherein the case has a substantially rectangular exterior cross section.

4. A syringe as in claim 1 for use by dental and medical practitioners wearing a surgical glove and wherein the plunger includes a ring intended to be engaged by a gloved hand of the user of the syringe, and wherein at least the ring as a color to blend with the color of said surgical glove.

5. A syringe as in claim 4 wherein the color is ivory.

6. A syringe as in claim 4 wherein the color of the ring is ivory.

7. A syringe as in claim 2 wherein the body and protector case are both injection molded from plastic.

8. A syringe as in claim 7 for use by dental and medical practitioners wearing a surgical glove and wherein at least a portion of the plunger has a color to blend with the color of said surgical glove.

9. A syringe as in claim 8 wherein the color is ivory.

10. A syringe as in claim 1 wherein the body is formed of clear plastic.

11. A syringe as in claim 1 for use by dental and medical practitioners wearing a surgical glove and wherein the plunger and plug have a color to blend with the color of said surgical glove.

12. A syringe as in claim 11 wherein the color is ivory.

13. A syringe as in claim 1 for use by dental and medical practitioners wearing a surgical glove and wherein the body and protector case have a color to blend with the color of said surgical glove.

14. A syringe as in claim 13 wherein the color is ivory.

15. A syringe as in claim 1 wherein at least a portion of the exterior of the syringe has an ivory color.

16. A disposable self-shielding aspirating syringe comprising a body having a cavity for receiving a medical carpule, the body having a first forward end for receiving a needle for penetrating a carpule and for injecting medicine into a patient, and the body having a second collar end into which the carpule can be inserted, and the body having a wall with an opening through which a carpule can be viewed, a protector case adapted to slidably fit on the body, and having a first open end through which a needle may extend and a second end wherein the second end of the case and the body have cooperating detents for facilitating placement of the case with respect to the body for uncovering and covering, respectively, an exposed end of a needle, and the case further comprising at least one elongated window opening for allowing the carpule to be viewed through the wall opening in the body through the window, the window having first and second ends, and the body having at least one tab for extending through and engaging at least one of the ends of the window, and a plunger assembly for cooperatively mating with the collar end of the body and comprising a movable plunger which is movable with respect to the body for causing medicine from the carpule to be administered through the needle.

17. A syringe as in claim 16 wherein the exterior of the body and the interior of the case each have a substantially rectangular cross-section.

18. A syringe as in claim 17 wherein the case has a substantially rectangular exterior cross section.

19. A syringe as in claim 16 for use by dental and medical practitioners wearing a surgical glove and wherein the body and protector case are both injection molded from plastic and have a color to blend with the color of said surgical glove.

20. A syringe as in claim 19 wherein the color is ivory.

21. A syringe as in claim 16 wherein at least a portion of the exterior of the syringe has an ivory color.

22. A disposable self-shielding aspirating syringe comprising a body formed of plastic having a cavity for receiving a medical carpule, and an open wall for allowing the carpule to be viewed through the body, the body having a first forward end with a needle for penetrating a carpule and for injecting medicine into a patient, the first end having fins for receiving a needle cover, and the body having a second collar end into which the carpule is inserted, a protector case adapted to slidably fit on the body, and having a first open end through which a needle may extend and a second end wherein the second end of the case and the body have cooperating detents for facilitating placement of the case with respect to the body for uncovering and covering, respectively, an exposed end of a needle, the detents comprising fingers on the cover for engaging slots in the body and the case further comprising an elongated window opening for allowing the carpule to be viewed in the body through the window, the window having first and second ends, and the body having a tab extending through the window for engaging an end of the window for limiting the relative travel of the case on the body, and a plug and plunger assembly comprising a plug for cooperatively mating with the collar end of the body and plunger which is movable with respect to the plug and body for causing medicine from the carpule to be administered through the needle.

23. A syringe as in claim 22 wherein the body and protector case are both injection molded from plastic.

24. A syringe as in claim 22 wherein the protector case is oriented with respect to the body such that the elongated window opening in the case is arranged to allow the carpule to be viewed in the body through the window when the case is placed with respect to the body for covering an exposed end of a needle but to not expose the carpule through the window when the case is placed with respect to the body for uncovering an exposed end of the needle.

25. A syringe as in claim 23 for use by dental and medical practitioners wearing a surgical glove and wherein the body and cover have a color to blend with the color of said surgical glove.

26. A syringe as in claim 25 wherein the color is ivory.

27. A syringe as in claim 22 wherein at least a portion of the exterior of the syringe has an ivory color.

28. A medical syringe including in combination a colored surgical glove for use by dental and medical practitioners wearing said surgical glove and for injecting medication into a body, comprising a syringe body and protector case movable with respect to the body to expose a needle for injection and to cover the needle for disposal, and wherein the syringe body and case are molded of plastic and further including a plunger assembly movable for causing medication to be injected and wherein at least one of the protector case and plunger assembly is of a color to blend with the color of said surgical glove.

29. A syringe as in claim 28 for use by dental and medical practitioners wearing a surgical glove and wherein the protector case has a color to blend with the color of said surgical glove.

30. A syringe as in claim 28 wherein the color is ivory.

31. A syringe as in claim 29 wherein the color is ivory.

32. A disposable self-shielding aspirating syringe comprising a body having a cavity for receiving a medical carpule, the body having a first forward end for receiving a needle for penetrating a carpule and for injecting medicine into a patient, and the body having a second collar end into which the carpule can be inserted, a protector case adapted to slidably fit on the body, and having a first open end through which a needle may extend and a second end wherein the second end of the case and the body have cooperating detents for facilitating placement of the case with respect to the body for uncovering and covering, respectively, an exposed end of a needle, and the case further comprising at least one elongated opening having first and second ends, and the body having at least one tab for extending through and engaging at least one of the ends of the elongated opening, and a plunger assembly for cooperatively mating with the collar end of the body and comprising a movable plunger which is movable with respect to the body for causing medicine from the carpule to be administered through the needle.

33. A syringe as in claim 32 wherein the exterior of the body and interior of the case each have a substantially rectangular cross-section, and wherein the body and protector case are both injection molded from a plastic having a substantially ivory color.

34. A syringe as in claim 32 wherein the first forward end of the body has a plurality of hub support vanes having edges with small radial protrusions thereon, and the first open end of the protector case has a like plurality of slots through which the edges of the vanes may extend and wherein the radial protrusions can provide an interference fit with an interior bore of a needle cap adapted to cover a needle extending through the first open end of the protector case.

35. A syringe comprising
a body having a cavity for receiving medicine, the body having a first forward end for receiving a needle for injecting medicine into a patient,
a protector case adapted to slidably fit on the body, and having a first open end through which a needle may extend and a second end wherein the second end of the case and the body have cooperating detents for facilitating placement of the case with respect to the body for uncovering and covering, respectively, an exposed end of a needle, and the case further comprising at least one elongated opening having first and second ends, and the body having at least one tab for extending through and engaging at least one of the ends of the elongated opening,
a plunger assembly for cooperatively mating with the second end of the body and comprising a movable plunger which is movable with respect to the body for causing medicine from the carpule to be administered through the needle, and
wherein the first forward end of the body has a plurality of hub support vanes having edges with small radial protrusions thereon, and the first open end of the protector case has a like plurality of slots through which the edges of the vanes may extend and wherein the radial protrusions can provide an interference fit with an interior bore of a needle cap adapted to cover a needle extending through the first open end of the protector case.

36. A syringe as in claim 35 wherein the exterior of the body and interior of the case each have a substantially rectangular cross-section, and wherein the body and protector case are both injection molded from a plastic.

37. A method of injecting medication into a body in a manner to be less obtrusive to a patient than through use of a conventional stainless steel aspirating syringe, comprising using a medical syringe having a syringe body and protector case movable with respect to the body to expose a needle for injection and to cover the needle for disposal, and wherein the syringe body and case are molded of a plastic and further including a plunger assembly movable for causing medication to be injected, and wherein at least one of the protector case and plunger is of a color which blends with the color of a surgical glove worn by a medical practitioner for performing the injection, the blending color of at least one of the protector case and plunger assembly and that of the surgical glove facilitating the less obtrusive appearance of at least a portion of the syringe to the patient.

* * * * *